(12) United States Patent
Royster (10) Patent No.: US 10,586,935 B2
(45) Date of Patent: Mar. 10, 2020

(54) BRIDGED BIS(AZINYL)AMINE PHOSPHORESCENT EMITTING COMPOSITIONS

(71) Applicant: Tommie L. Royster, Webster, NY (US)

(72) Inventor: Tommie L. Royster, Webster, NY (US)

(73) Assignee: R-Display & Lighting, LLC, Webster, NY (US)

( * ) Notice: Subject to any disclaimer, the term of this patent is extended or adjusted under 35 U.S.C. 154(b) by 0 days.

(21) Appl. No.: 16/207,969

(22) Filed: Dec. 3, 2018

(65) Prior Publication Data

US 2019/0173026 A1 Jun. 6, 2019

Related U.S. Application Data

(60) Provisional application No. 62/594,413, filed on Dec. 4, 2017.

(51) Int. Cl.
| | |
|---|---|
| C09K 11/06 | (2006.01) |
| H01L 51/50 | (2006.01) |
| H01L 51/00 | (2006.01) |
| C07F 15/00 | (2006.01) |

(52) U.S. Cl.
CPC ...... *H01L 51/0087* (2013.01); *C07F 15/0093* (2013.01); *C09K 11/06* (2013.01); *C09K 2211/1022* (2013.01); *C09K 2211/1029* (2013.01); *C09K 2211/185* (2013.01); *H01L 51/5004* (2013.01); *H01L 51/5016* (2013.01); *H01L 2251/552* (2013.01)

(58) Field of Classification Search
CPC .......................... C07F 15/0086; H01L 51/5012
USPC .................... 546/2, 10; 313/504; 252/301.26
See application file for complete search history.

(56) References Cited

U.S. PATENT DOCUMENTS

| | | | |
|---|---|---|---|
| 6,303,238 B1 | 10/2001 | Thompson et al. | |
| 6,661,023 B2 | 12/2003 | Hoag et al. | |
| 6,830,828 B2 | 12/2004 | Thompson et al. | |
| 7,063,901 B2 | 6/2006 | Igarashi et al. | |
| 9,118,024 B2 | 8/2015 | Royster | |
| 2010/0213824 A1 | 8/2010 | Adler et al. | |
| 2013/0168656 A1 | 7/2013 | Tsai et al. | |
| 2015/0349279 A1 | 12/2015 | Li et al. | |
| 2016/0028028 A1 | 1/2016 | Li et al. | |
| 2017/0174985 A1 | 6/2017 | Royster | |

FOREIGN PATENT DOCUMENTS

| | | |
|---|---|---|
| JP | 2004-296170 A | 10/2004 |
| JP | 2010-135689 A | 6/2010 |
| KR | 10-2007-0081406 A | 8/2007 |
| KR | 10-2008-0046698 A1 | 5/2008 |

OTHER PUBLICATIONS

Furuhama, A. et al.: A theoretical study of tautomerism in hexa-aza macrocycles containing 2, 2'-bipyridine and 1, 10-phenanthroline and their ability to form lithium complexes. Journal of Molec. Structure, vol. 620, pp. 49-63, 2003.*

Tetradendate Pt(II) Complexes with 6-Membered Chelate Rings: A New Route for Stable and Efficient Blue Organic Light Emitting Diodes, Tyler B. Fleetham, Liang Huang, Kody Klimes, Jason Brooks, and Jian Li, Article, Chem. Mater. 2016, 28, 3276-3282, US.

Emission Studies of Transition-Metal Complexes of 2,2'-Dipyridylamine. BisComplexes of Rhodium(III) and Irdiium(III), Wen Liang Huang, Donald P. Segers, and M. Keith Dearmond, Article, J. Phys. Chem. 1981, 85, 2080-2086, US.

Platinum Complexes Bearing 2,2'-Dipyridylamine Ligand, Q. Wang, P. V. Gushchin, N.A. Bokach, M. Haukka, and V. YU. Kukushkin, Russian Chemical Bulletin, International Edition, vol. 61, No. 4, pp. 828-835, Apr. 2012.

International Search Report for application PCT/US2018/063598, Korean Intellectual Property Office, dated Apr. 5, 2019.

* cited by examiner

*Primary Examiner* — Charanjit Aulakh
(74) *Attorney, Agent, or Firm* — Hodgson Russ LLP (57) ABSTRACT

A light emitting composition comprising a central platinum group transition metal coordinated to a bridged tetradentate ligand comprised of chelating bis(azinyl)amine groups. A six-membered heteroatom ring is formed through coordination of the chelating ligand with the transition metal. An electron donating moiety serves as a bridge between the bis(azinyl)amine groups. The electron donating moiety can include amine or aryl groups. The platinum group transition metal may be selected from the group consisting of platinum, palladium, iridium, rhodium, ruthenium, and osmium. Additionally, OLED devices are provided, each of the OLED devices comprising a light emitting layer that includes one of the light emitting compositions.

12 Claims, 8 Drawing Sheets

PRIOR ART

GENERAL STRUCTURES

R = H, alkyl or aryl groups
R' = alkyl or aryl groups
M = Platinum Group Metal
L = monodentate or bidentdate ligand
n = 0 or 1

PREFERRED
EMBODIMENTS

BRIDGED BIS(AZINYL)AMINE PHOSPHORESCENT EMITTING COMPOSITIONS

CROSS-REFERENCE TO RELATED PATENT APPLICATIONS

This application claims the benefit of U.S. Provisional Patent Application No. 62/594,413 filed Dec. 4, 2017, the disclosure(s) of which is/are incorporated herein by reference. The above benefit claim is being made in an Application Data Sheet submitted herewith in accordance with 37 C.F.R. 1.76 (b)(5) and 37 C.F.R. 1.78.

BACKGROUND

Technical Field

Light-emitting compositions of matter. In particular, highly efficient phosphorescent emitter compositions that are useful in organic light emitting diodes.

Description of Related Art

Figure 1:
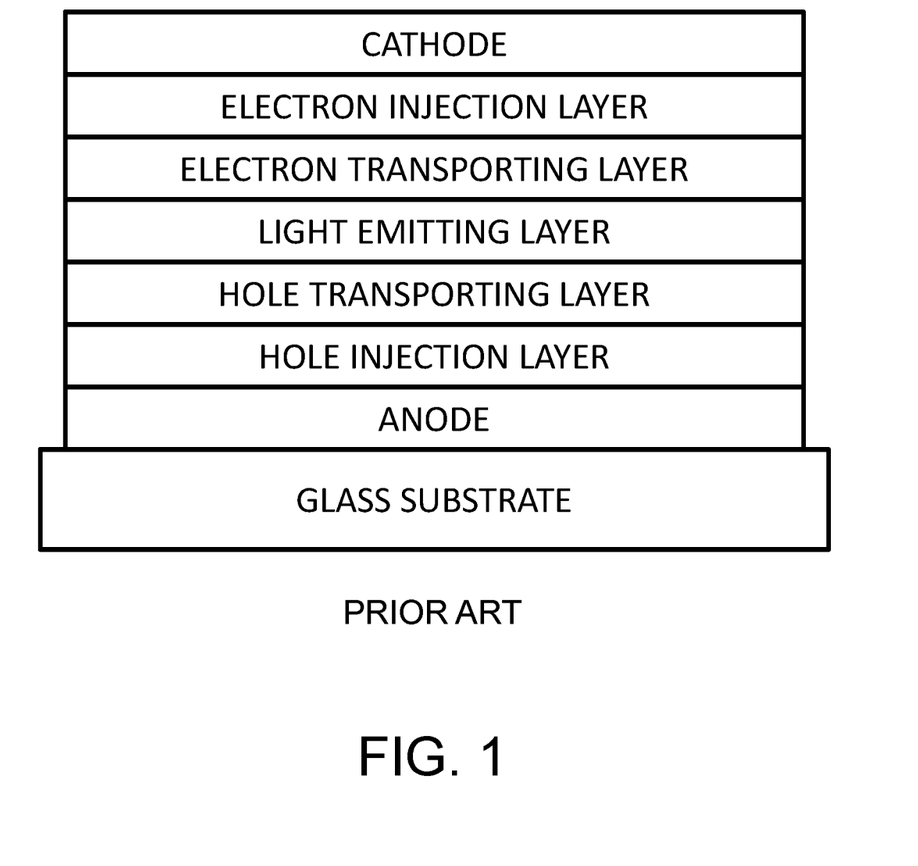
FIG. 1 is a schematic illustration of the layered structure of an organic light emitting diode.

Organic Light Emitting Diode (OLED) devices are based on strategic placement of organic thin films between electrodes (i.e. an anode and a cathode). The basic structure of an OLED device is shown in FIG. 1. Injection of holes and elections from the anode and cathode result in light emission through recombination of the holes and electrons in the light emitting layer of the "organic stack," which is the set of layers between the anode and the cathode. The organic thin films in an OLED device are typically less than 50 nanometers (nm) in thickness, resulting in low voltage operations and potential to produce low power consuming devices. These attributes are advantageous in the use of OLED devices in image display and lighting applications.

Figure 2:
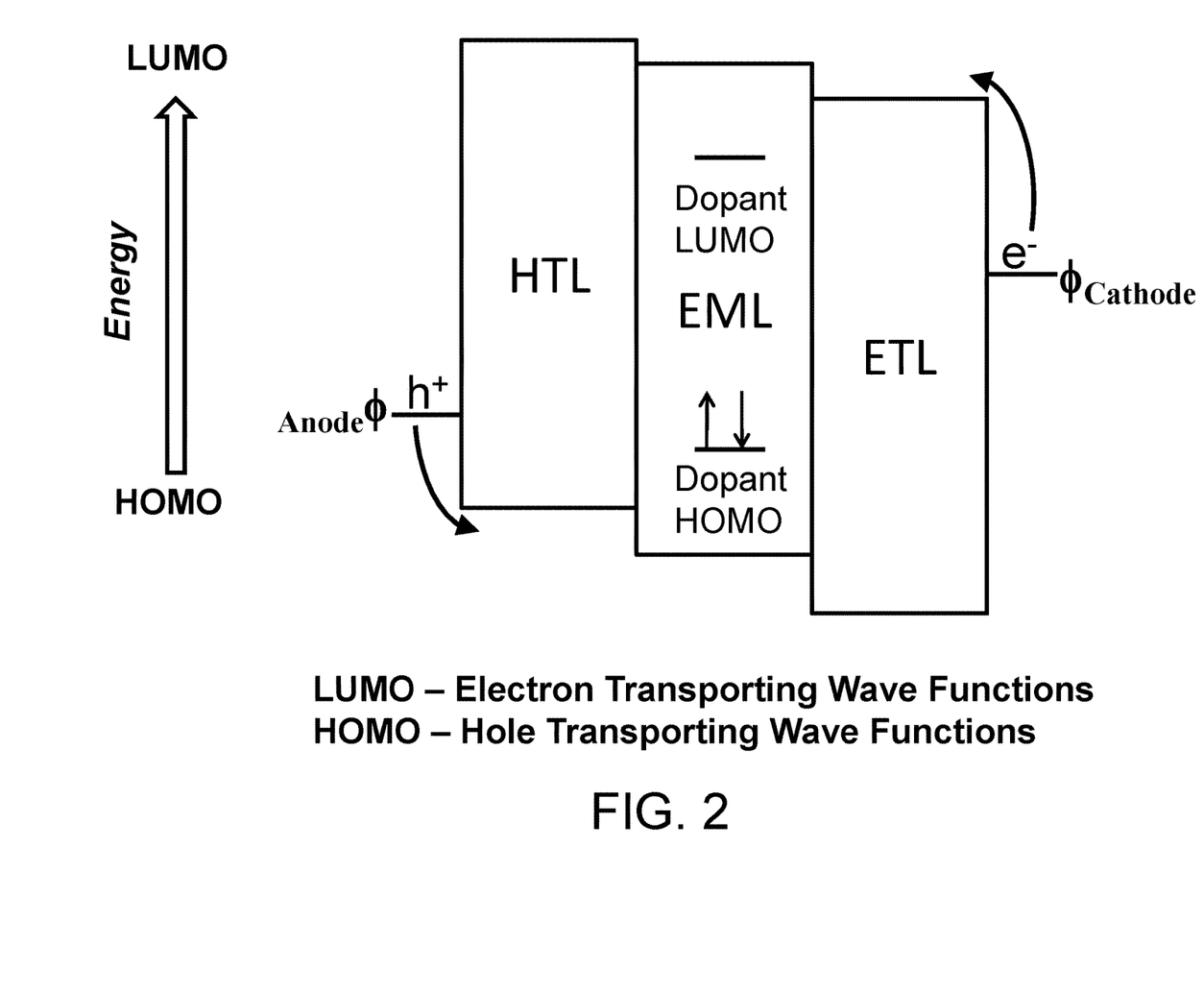
FIG. 2 is a schematic illustration of the hole/electron injection process in the generation of light by an organic light emitting diode.
Figure 3:
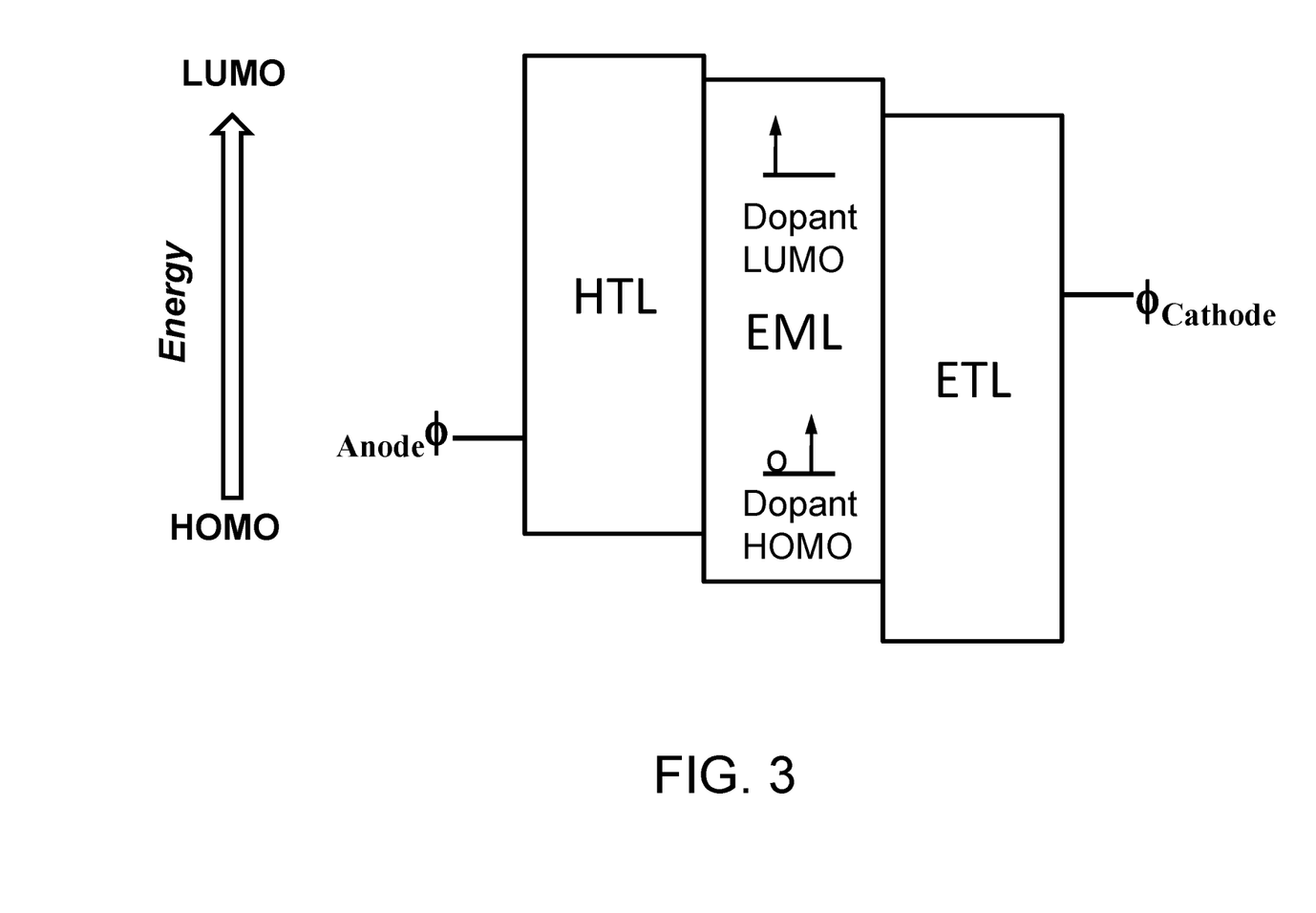
FIG. 3 is a schematic illustration of the triplet exciton formation process in the generation of light by an organic light emitting diode.
Figure 4:
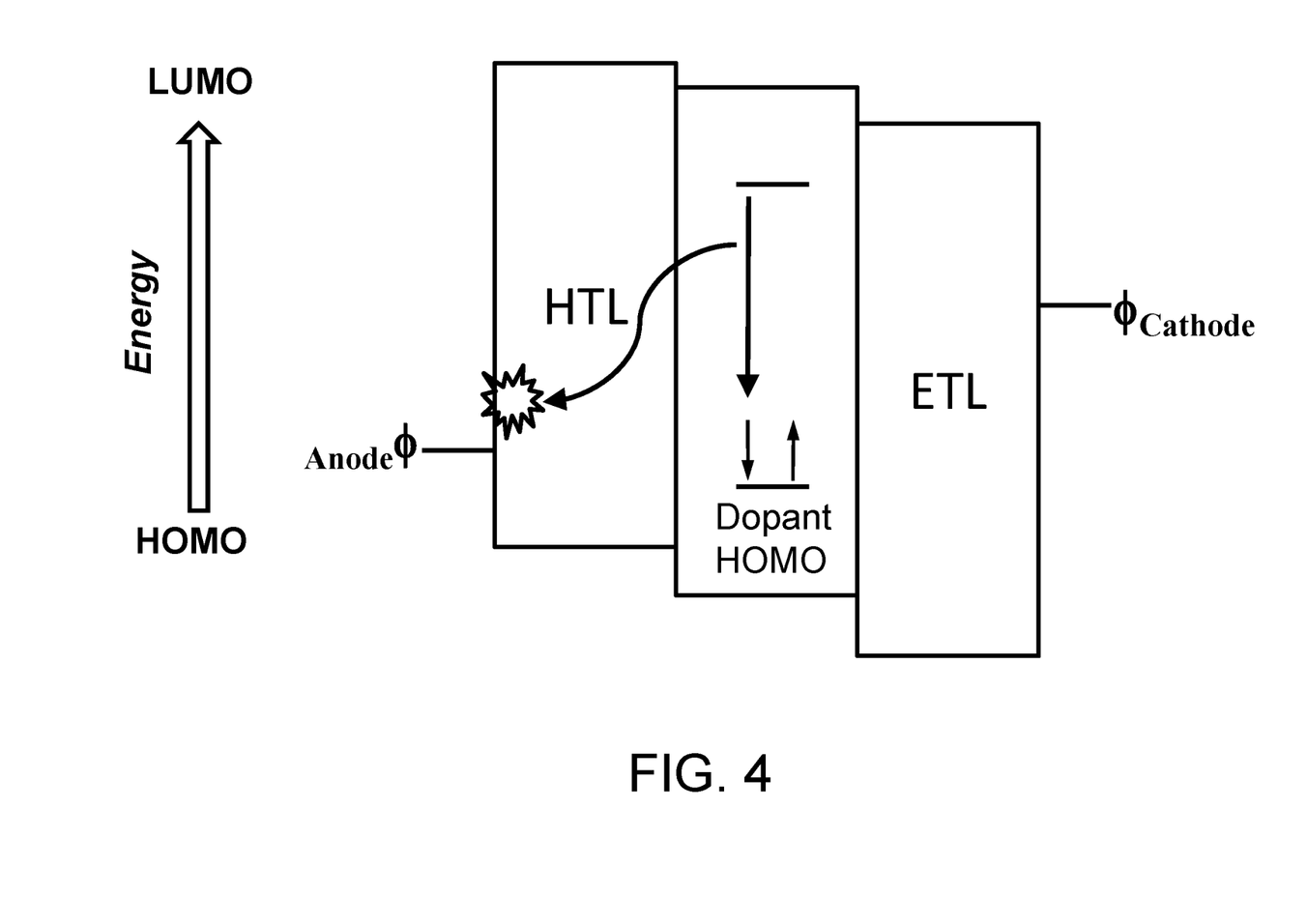
FIG. 4 is a schematic illustration of the subsequent exciton decay process in the generation of light by an organic light emitting diode.

The excited states generated from hole and electron injection setup two pathways for light emission. Singlet and Triplet exciton decay yield fluorescent and phosphorescent light respectively. The ratio of Singlet to Triplet exciton formation is 1:3. Therefore, emissive layers comprised of fluorescent dopant and host materials for harvesting singlet excitons have a theoretical limit of 25% for converting excitons into light. However, phosphorescent systems can theoretically convert 100% of the excitons generated into light by harvesting Singlet excitons (after intersystem conversion) and Triplet excitons. Emissive layers are comprised of a host material and a phosphorescent dopant. Steps representing the hole/electron injection process, Triplet exciton formation and subsequent exciton decay to produce light are depicted in FIGS. 2-4.

The high efficiency of phosphorescent based OLED devices establishes a platform for manufacturing very low power consuming lighting and display applications. Based on the high efficiency, lower driving currents are required for light output, thereby establishing the potential for significant savings in power consumption. The shift from fluorescent based OLED devices to phosphorescent based devices in commercial applications has commenced. However, there are still problems that remain to be solved for broader application of phosphorescent based OLED devices to occur.

OLED displays have evolved from exclusive use of fluorescent emitter materials to incorporating more device efficient phosphorescent materials currently found in state-of-the art displays for smart phones and select HD-TV's. Specifically, red and green fluorescent emitters have been replaced with red and green phosphorescent emitters. A blue phosphorescent dopant has yet to be discovered that meets the industry requirements for color and device stability. This technology gap represents a major innovation opportunity for OLED emitter materials.

Calculations from at least two independent studies predict the neutral metal-nitrogen bond in cyclometalated complexes ruptures upon absorption of high energy light or thermal activation in the Triplet excited state. Regardless of the degradation mechanism, current blue phosphorescent emitter materials lack the desired stability that would enable commercialization of a blue phosphorescent emitter. Therefore, a need remains for blue phosphorescent emitter materials that operate in an OLED device at high efficiency, and improved stability.

SUMMARY

A new class of phosphorescent emitter materials have been designed and developed which produces phosphorescent light with CIE 1931 color coordinates that cover visible light from red to deep blue.

More particularly, in accordance with the present disclosure, a light emitting composition is provided comprising a central platinum group transition metal coordinated to a bridged tetradentate ligand comprised of chelating bis(azinyl)amine groups. A six-membered heteroatom ring is formed through coordination of the chelating ligand with the transition metal. An electron donating moiety serves as a bridge between the bis(azinyl)amine groups. The electron donating moiety can include amine or aryl groups. The platinum group transition metal may be selected from the group consisting of platinum, palladium, iridium, rhodium, ruthenium, and osmium. Additionally, in accordance with the present disclosure, OLED devices are provided, each of the OLED devices comprising a light emitting layer that includes one of the light emitting compositions.

DETAILED DESCRIPTION

The present invention will be described in connection with certain preferred embodiments. However, it is to be understood that there is no intent to limit the invention to the embodiments described. On the contrary, the intent is to cover all alternatives, modifications, and equivalents as may be included within the spirit and scope of the invention as defined by the appended claims.

For a general understanding of the present invention, reference is made to the drawings. The drawings are to be considered as depicting exemplary embodiments of the invention, and not to be considered as limiting the invention solely to the embodiments depicted.

Figure 5A:
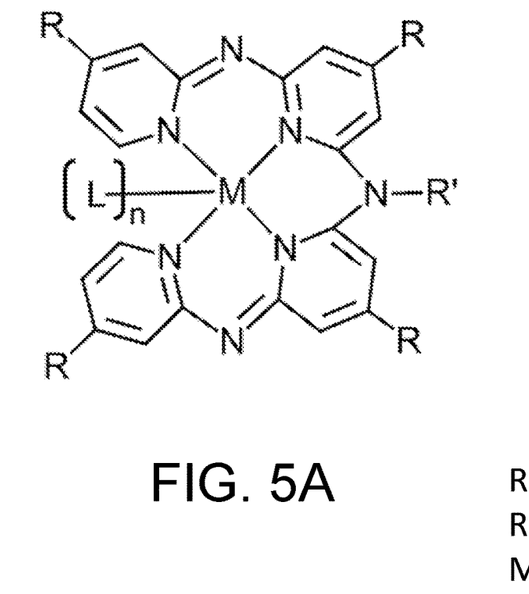
FIG. 5A is an illustration of the general chemical structure of a first generic light-emitting composition of the present disclosure.
Figure 5B:
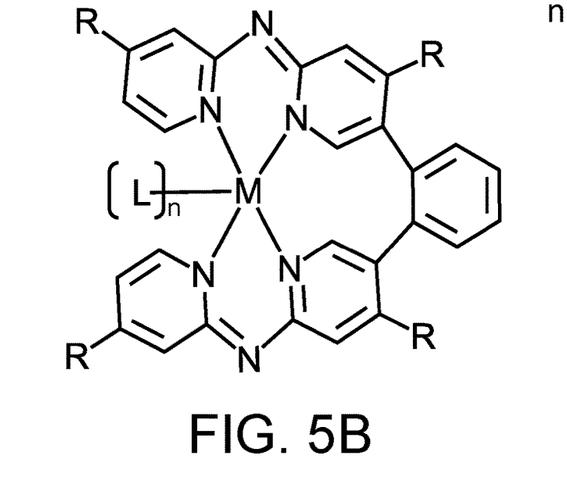
FIG. 5B is an illustration of the general chemical structure of a second generic light-emitting composition of the present disclosure.
Figure 6:
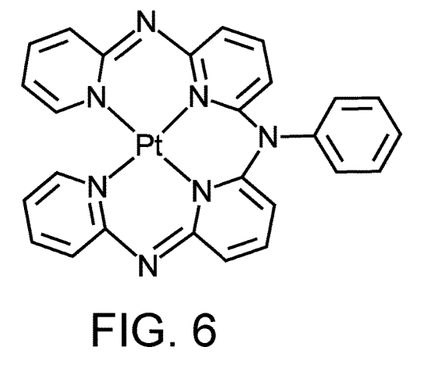
FIG. 6 is an illustration of the chemical structure of a first exemplary light-emitting composition of the present disclosure.
Figure 7A:
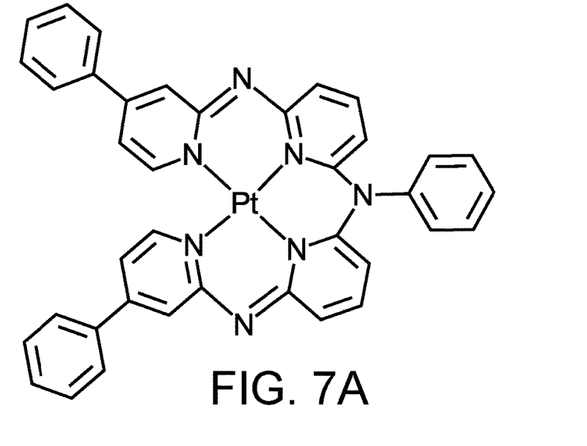
FIG. 7A-7F are illustrations of the chemical structures of additional exemplary light-emitting compositions of the present disclosure.
Figure 7B:
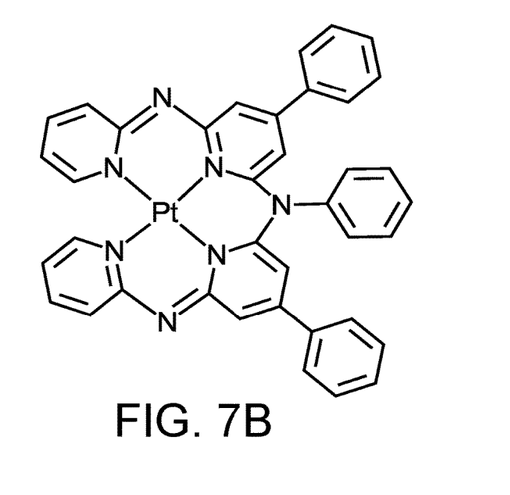
Figure 7C:
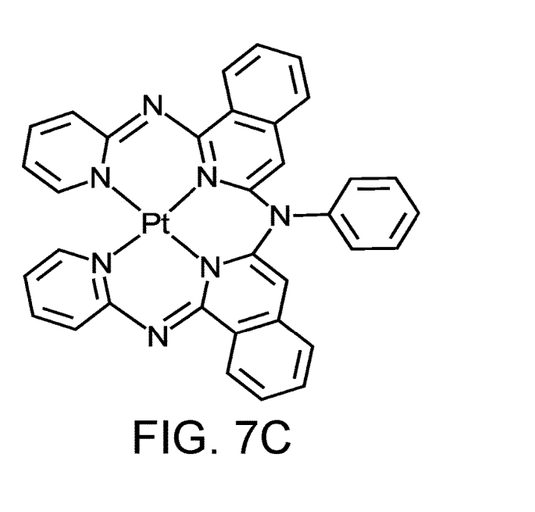
Figure 7D:
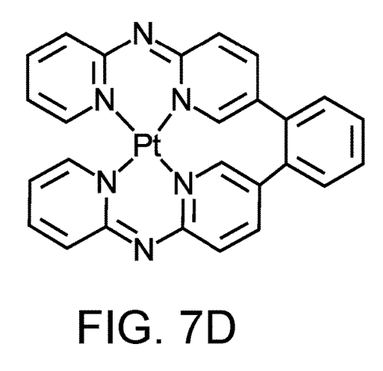
Figure 7E:
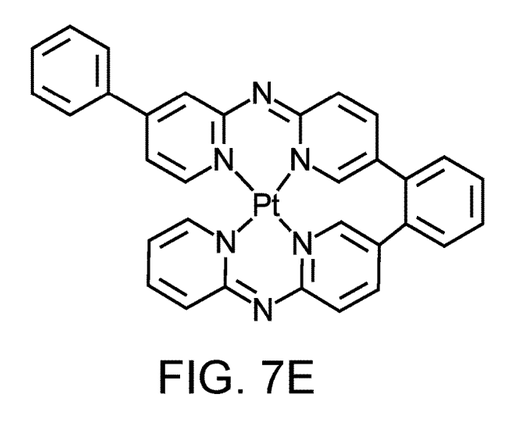
Figure 7F:
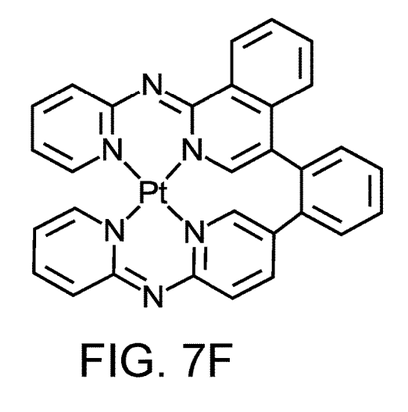

Through a combination of synthetic and photoluminescence studies, the Applicant has discovered a new class of phosphorescent emitter material compositions that provide high efficiency and broad color tuning capability. General structures of the new class of compositions are shown in FIGS. 5A and 5B. Referring to FIG. 5A, the structure of the "generic composition" includes a central platinum group transition metal coordinated to a tetradentate ligand comprised of chelating bis(azinyl)amine groups linked through a bridging electron donating moiety. The electron donating moiety can include amine or aryl groups. An additional general structure of the is shown in FIG. 5B. Preferred embodiments of the invention are shown in FIGS. 6, and 7A-7D.

EXAMPLES

Example 1. Synthesis of 2-{N-Phenyl[6-(2-pyridylamino)-2-pyridyl]amino}-6-(2-pyridylamino)pyridine The ligand precursor to the light emitting compound of FIG. 6 was prepared according to the following procedure: To a 500 mL round-bottom flask 12 g (81 mmol) of 2,6 dichloropyridine, 2.5 g (27 mmol) of aniline, 7.3 g (76 mmol) of sodium tert-butoxide and Bis(diphenylphosphino) ferrocene]dichloropalladium(II)*CH$_2$Cl$_2$, 2.2 g (2.7 mmol) was added followed by 125 mL of anhydrous Toluene. The reaction mixture was heated at 105° C. for ~36 h under nitrogen in the Rotavisse joint sealed reaction flask.

The solution was filtered and the filtrate and insolubles were analyzed by liquid chromatography-mass spectrometry (LC-MS). The desired dichloro intermediate compound was detected in both the filtrate and insolubles as the primary product. The insoluble material was recombined with the filtrate before removing the solvent using the rotary evaporator.

The product was washed with washed water and then dried under vacuum using an oil bath to heat the flask.

Working in a drybox, the dichloro intermediate product was transferred to a clean Schlenk flask with Toluene. To the flask was added ~6.5 g of 2-aminopyridine, ~1.7 g of the Pd complex and additional sodium tert-butoxide (~7.0 g). A total of 150 mL of Anhydrous Toluene was added. The flask was sealed, taken from the drybox and placed in an oil bath. The flask was heated to 128° C. for less than 24 hours before lowering the temperature to ~120° C. After 36 hrs, the heat was removed. Upon cooling, the solution was filtered to remove insoluble and the precipitate washed with additional Toluene. The solvent was evaporated from the filtrate leaving a brown viscous product. The product was heated under vacuum over to night to remove excess solvent and starting material 2-aminopyridine which sublimes at 110° C. A total of 9.38 g (81% yield) of crude product was isolated. Purification before used was achieved through an acetone wash followed by sublimation.

Example 2. General Method of Pt Complex Preparation

The following description is provided as an example of a general method of the steps of coordinating a central platinum group transition metal to a bridged tetradentate ligand to form the phosphorescent emitter materials of the present disclosure.

In a general reaction, 3 mmol of the Pt complex K$_2$PtCl$_4$ was weighed out and transferred to a reaction flask. High purity water (8 mL) was then added to the flask and the solution stirred to dissolve the Pt salt. While stirring, 30 mL of methanol was added followed by the addition of the solid bis(azinyl)amine chelating ligand (6 mmol). An additional 5 mL of the solvent was used to rinse down any remaining ligand. After purging the flask with nitrogen, the flask was sealed with a Rodavise cap (a condenser with a nitrogen bubbler can also be used).

The reaction was heated (75-80° C.) in an oil bath. After 10-16 hours, the heat was removed and the reaction flask allowed to cool to room temperature. Additional methanol and water was added (60 mL and 20 mL respectively). While stirring, 20 mL of an aqueous solution with excess KOH was added dropwise. The solution was again purged with nitrogen before stirring for 2-3 hours with low heat. The solvent volume was reduced before introducing additional water. The product was allowed to settle before collecting by filtration. The product was confirmed by LC-MS analysis to be the composition shown in FIG. 6, before purification by sublimation.

Example 3. OLED Device Comprised of Exemplary Emitter Composition

A glass substrate coated with about a 21.5 nm layer of indium-tin oxide (ITO), as the anode, was sequentially washed in a commercial detergent, rinsed in deionized water, rinsed with acetone, and exposed to an oxygen-plasma for about 1 min. Over the ITO, a 10 nm thick hole-injecting layer (HIL), LG-101, manufactured and sold by LG Chem Corporation of Seoul, South Korea, was vapor deposited. Next, a layer of a Hole Transporting Material, was deposited to a thickness of 50 nm following by 10 nm of N,N'-Dicarbazolyl-3,5-benzene as the Exciton blocking layer. A 30 nm light-emitting layer (LEL) comprising 3,3-Di(9H-carbazol-9-yl)biphenyl as the host and the Exemplary Composition represented in FIG. 6 (4%) was then deposited. A 20 nm layer hole blocking layer material was deposited for the electron-transporting layer corresponding to 20 nm. A 0.5 nm layer of electron-injecting layer lithium fluoride was deposited and finally, a 125 nm layer of aluminum was deposited to form a cathode layer. An electroluminescence spectrum recorded from the device is shown in FIG. 8.

Figure 8:
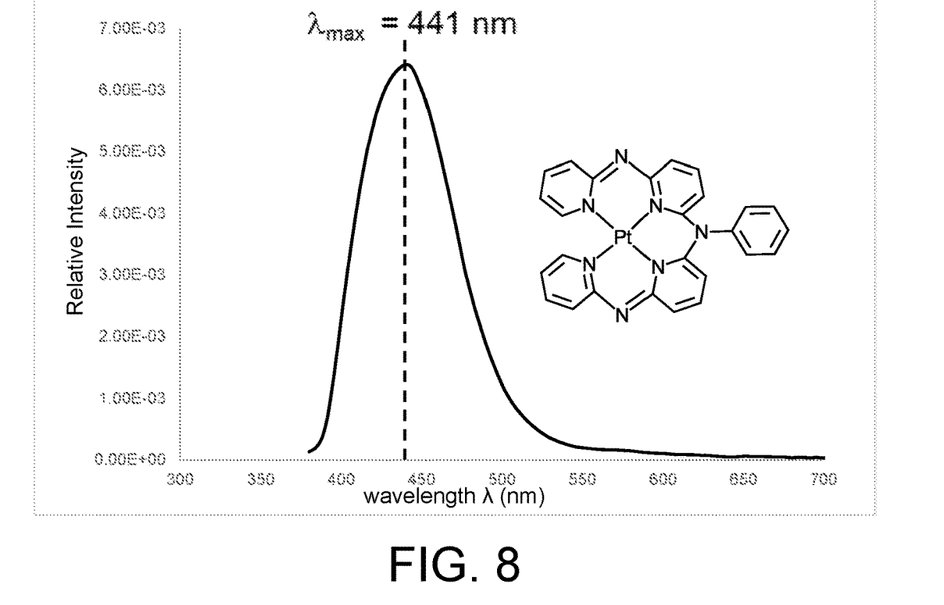
FIG. 8 is an electroluminescence spectrum of an OLED device comprised of the exemplary emitter composition of FIG. 6.
Figure 9:
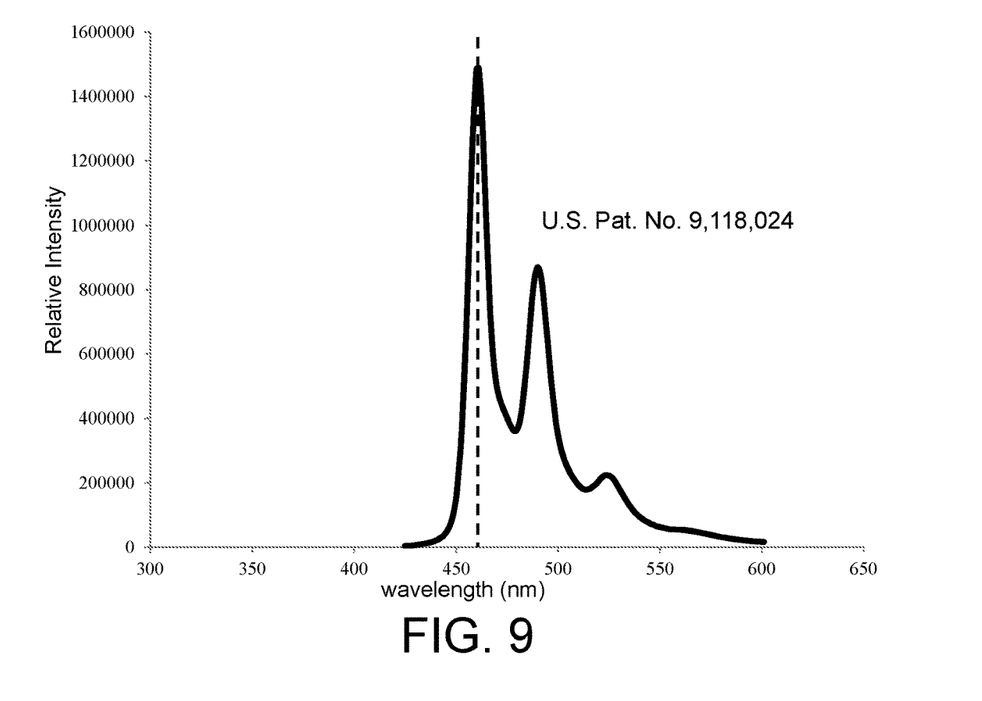
FIG. 9 is an electroluminescence spectrum of an OLED device as disclosed in U.S. Pat. No. 9,118,024.

The unique light emission band that is observed and shown in FIG. 8 establishes an unexpected advantage for producing deep blue light. For comparison, FIG. 9 shows an emission band of a previous OLED composition disclosed in U.S. Pat. No. 9,118,024, the disclosure of which is incorporated herein by reference. The emission band of FIG. 9 is the emission band of the composition of FIG. 10 of the '024 patent, as shown in FIG. 18 of the '024 patent. By comparing the two emission bands, it can be seen that the emission band shape of the composition of FIG. 6, as shown in FIG. 8, is not typical for blue fluorescent or phosphorescent emitter materials.

This is illustrated by drawing a vertical line at the emission maximum position through the emission bands of the invention (FIG. 8) and the previously disclosed reference fluorescent blue emitter of the '082 patent (FIG. 9). From a comparison of the emission bands, it can be seen that the emission band for the OLED device of the present invention has close to equal distribution of light on the short and long wavelength sides of the emission maximum. In contrast, the OLED composition of the '082 patent exhibits light emission primarily on the long wavelength side of the emission maximum. The higher production of light by the OLED device of the present invention on the short wavelength side provides a distinct advantage for production of deep blue light for electroluminescence devices as indicated by the CIE x,y coordinates represented in Table 1. The table also provides the luminous efficacy data for the blue OLED device.

TABLE 1

Electroluminescence spectrum of exemplary OLED device

| Luminous Efficacy (lm/W-Light) | CIEx, y 1931 |
|---|---|
| 63 | 0.16, 0.07 |

Referring again to FIG. 8, in certain embodiments, OLEDS made with the light emitting compositions of the present disclosure may have about 20-60% of the generated light originating from the short wavelength side of the emission maximum.

It is therefore apparent that there has been provided, in accordance with the present disclosure, new compositions of phosphorescent emitter materials, methods of synthesizing such materials, and OLED devices comprised of such materials that produce unique emission band features.

The foregoing description of technology and the invention is merely exemplary in nature of the subject matter, manufacture, and use of the invention and is not intended to limit the scope, application, or uses of any specific invention claimed in this application or in such other applications as may be filed claiming priority to this application, or patents issuing therefrom. The following definitions and non-limiting guidelines must be considered in reviewing the description.

The headings in this disclosure (such as "Background" and "Summary") and sub-headings used herein are intended only for general organization of topics within the present technology, and are not intended to limit the disclosure of the present technology or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

To the extent that other references may contain similar information in the Background herein, said statements do not constitute an admission that those references are prior art or have any relevance to the patentability of the technology disclosed herein. Any discussion in the Background is intended merely to provide a general summary of assertions.

The description and specific examples, while indicating embodiments of the technology disclosed herein, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

To the extent employed herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the words "comprise," "include," contain," and variants thereof are intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Having thus described the basic concept of the invention, it will be apparent to those skilled in the art that the foregoing detailed disclosure is intended to be presented by way of example only, and is not limiting. Various alterations, improvements, and modifications will occur to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be expressly stated in the claims.

I claim:

1. A light emitting composition, wherein the composition has the general structure:

wherein R is selected from hydrogen, an alkyl group, and an aryl group; R' is selected from an alkyl group and an aryl group; M is the central platinum group transition metal; L is selected from a monodentate ligand and a bidentate ligand; and n=0 or 1.

2. The composition of claim 1, wherein the composition has the structure:

3. The composition of claim 1, wherein the composition has the structure:

4. The composition of claim 1, wherein the composition has the structure:

5. A light emitting composition, wherein the composition has the general structure:

wherein R is selected from hydrogen, an alkyl group, and an aryl group; M is the central platinum group transition metal; L is selected from a monodentate ligand and a bidentate ligand; and n=0 or 1.

6. The composition of claim 5, wherein the composition has the structure:

7. The composition of claim 5, wherein the composition has the structure:

8. An OLED device comprising a light emitting layer including a light emitting composition, wherein the composition has the general structure:

wherein R is selected from hydrogen, an alkyl group, and an aryl group; R' is selected from an alkyl group and an aryl group; M is the central platinum group transition metal; L is selected from a monodentate ligand and a bidentate ligand; and n=0 or 1.

9. An OLED device comprising a light emitting layer including a light emitting composition, wherein the composition has the general structure:

wherein R is selected from hydrogen, an alkyl group, and an aryl group; M is the central platinum group transition metal, L is selected from a monodentate ligand and a bidentate ligand; and n=0 or 1.

10. The OLED device of claim 8, operable to emit light from an electroluminescence band having a maximum intensity at a central wavelength, and between 20 and 60% of generated light originating from wavelengths less than the emission maximum.

11. A light emitting composition, wherein the composition has the structure:

12. A light emitting composition, wherein the composition has the structure:

* * * * *